(12) United States Patent
Berghausen

(10) Patent No.: US 7,531,650 B2
(45) Date of Patent: May 12, 2009

(54) CEPHALOSPORIN SALTS IN CRYSTALLINE FORM

(75) Inventor: Joerg Berghausen, Lörrach (DE)

(73) Assignee: Basilea Pharmaceutica AG, Basel (CH)

( * ) Notice: Subject to any disclaimer, the term of this patent is extended or adjusted under 35 U.S.C. 154(b) by 220 days.

(21) Appl. No.: 10/547,648

(22) PCT Filed: Mar. 15, 2004

(86) PCT No.: PCT/EP2004/002667

§ 371 (c)(1),
(2), (4) Date: Sep. 1, 2005

(87) PCT Pub. No.: WO2004/085444

PCT Pub. Date: Oct. 7, 2004

(65) Prior Publication Data

US 2006/0167242 A1      Jul. 27, 2006

(30) Foreign Application Priority Data

Mar. 27, 2003   (EP)   ................... 03006815

(51) Int. Cl.
*C07D 501/24*   (2006.01)
(52) U.S. Cl. .................................. 540/222
(58) Field of Classification Search ............... 540/222; 514/202
See application file for complete search history.

(56) References Cited

U.S. PATENT DOCUMENTS

| | | | | |
|---|---|---|---|---|
| 3,686,168 A | * | 8/1972 | Timreck | 540/320 |
| 3,697,506 A | * | 10/1972 | Butler | 540/320 |
| 4,411,897 A | | 10/1983 | Scartazzini | |
| 4,432,987 A | * | 2/1984 | Barth et al. | 514/193 |
| 4,634,556 A | * | 1/1987 | Jenkins et al. | 540/310 |
| 4,978,752 A | * | 12/1990 | Maeda et al. | 540/222 |
| 5,095,011 A | * | 3/1992 | Kaplan et al. | 514/202 |
| 5,492,903 A | * | 2/1996 | Maeda et al. | 514/195 |
| 5,721,359 A | * | 2/1998 | Dunn et al. | 540/227 |
| 6,232,306 B1 | | 5/2001 | Hebeisen et al. | |
| 6,441,162 B2 | * | 8/2002 | Yasui et al. | 540/227 |
| 6,504,025 B2 | * | 1/2003 | Hebeisen et al. | 540/222 |
| 7,145,002 B2 | * | 12/2006 | Brands et al. | 540/350 |

FOREIGN PATENT DOCUMENTS

| | | |
|---|---|---|
| EP | 0102896 | 3/1984 |
| EP | 0363826 | 4/1990 |
| EP | 0849269 | 6/1998 |
| EP | 1087980 A1 | 4/2001 |
| WO | WO 01/90111 | 11/2001 |

OTHER PUBLICATIONS

The Examination Report by the European Patent Office, issued on Nov. 14, 2006, in the European application No. 04720595.0.
The Indian Office Action, issued on Jul. 28, 2008, in the corresponding Indian application No. 2774/CHENP/2005.

* cited by examiner

*Primary Examiner*—Mark L Berch

(57) ABSTRACT

The present invention relates to cephalosporin of formula (I) in crystalline form. The compound of formula (I) in crystalline form is useful as antibiotics having potent and broad antibacterial activity; especially against methicillin resistant *Staphylococci* (MRSA) and *Pseudomonas aeruginosa*.

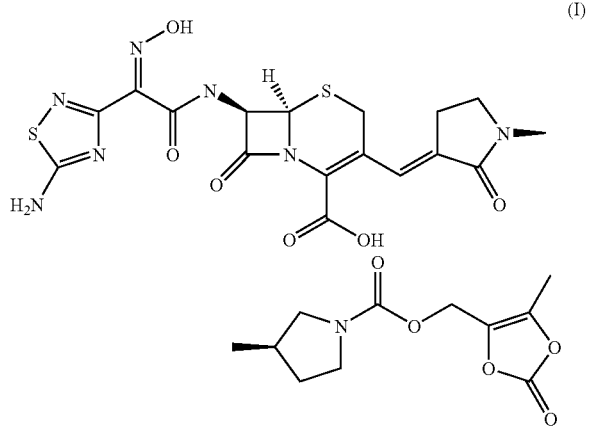

(I)

6 Claims, 1 Drawing Sheet

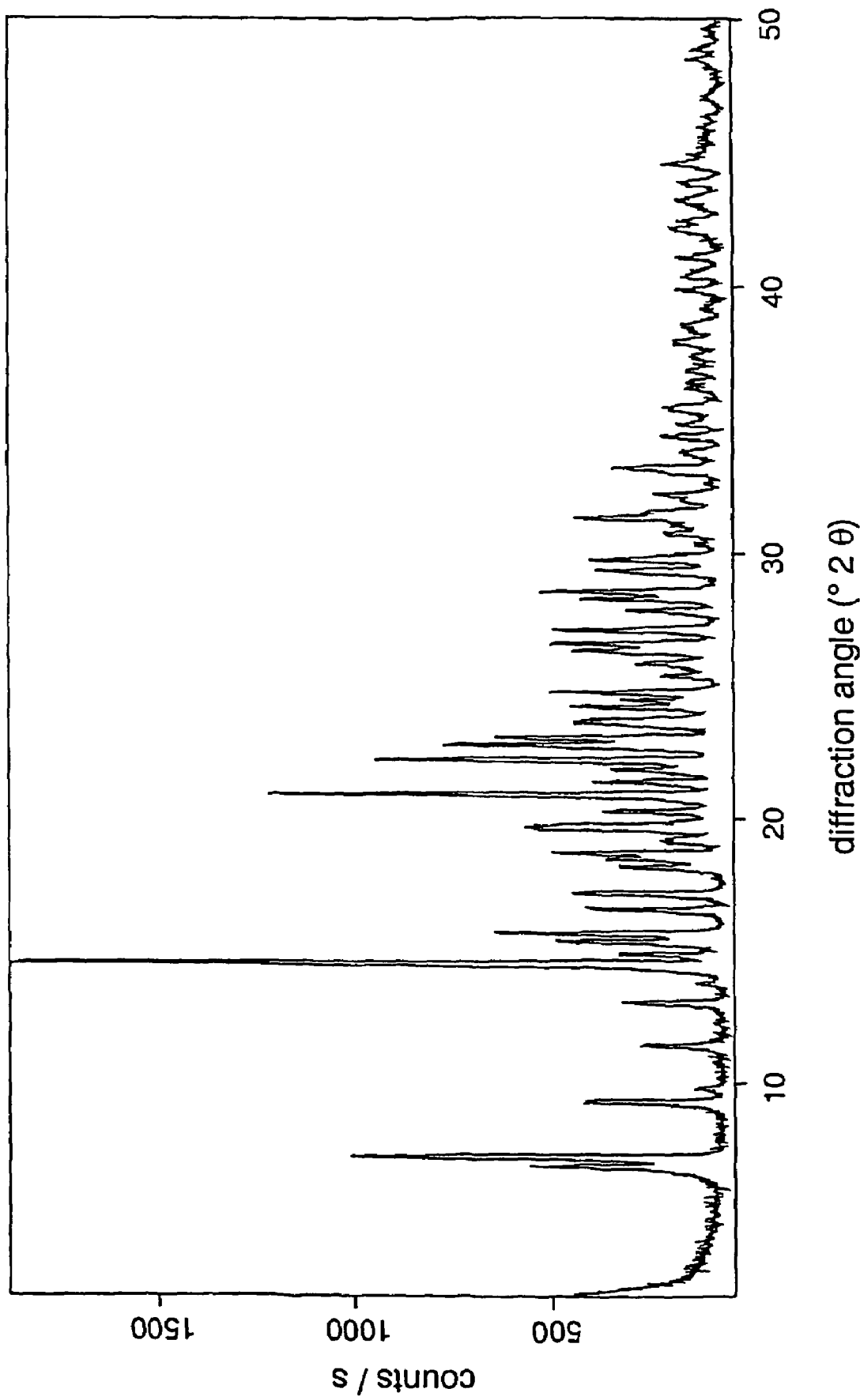
Figure 1: Powder X-ray Diffraction Pattern of crystalline form of cephalosporin of formula II (CuKα radiation)

CEPHALOSPORIN SALTS IN CRYSTALLINE FORM

The present invention relates to cephalosporin in crystalline form and a process for its preparation. Further, the present invention relates to the use of said cephalosporin in crystalline form alone or in combination with other compounds or formulations of said cephalosporin in crystalline form as antibiotic compounds.

The cephalosporin of formula I

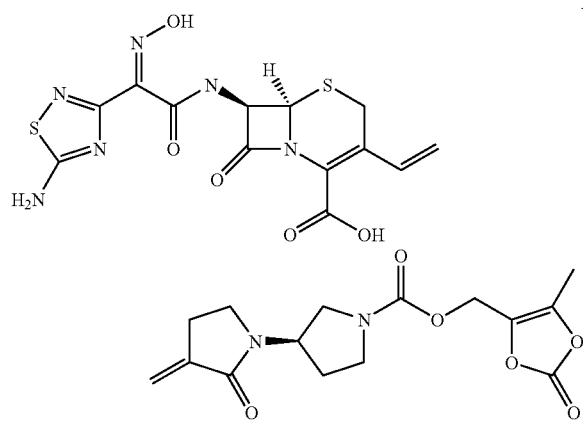

as well as the process for its preparation of the amorphous form is know from EP 1087980 and EP 0849269.

The cephalosporin of the above formula and its sodium salt (cephalosporin of formula III) have the disadvantage of low stability due to their amorphous form. The problem to be solved by the present invention was to provide a cephalosporin in a more stable form.

An object of the present invention is to provide cephalosporin of formula I in crystalline form which have a higher stability.

It has been surprisingly found that a cephalosporin salt in the form of stable crystals can be obtained by crystallizing a cephalosporin in the presence of an acid.

The present invention relates to cephalosporin of formula I in crystalline form

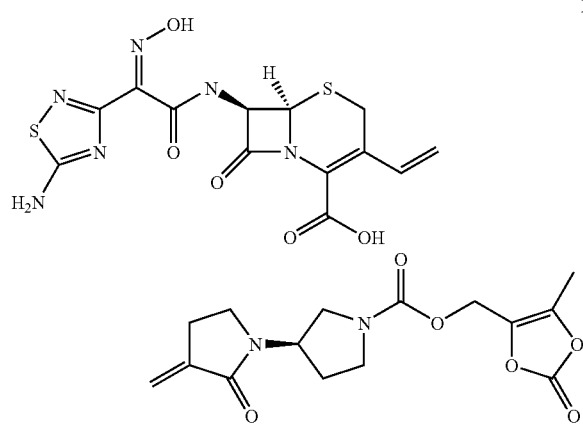

Further, the present invention relates to cephalosporin of formula I, which is a hydrochloride hydrate.

The present invention also relates to cephalosporin of formula I, which is a hydrobromide or hydrobromide hydrate.

Further, the present invention relates to cephalosporin of formula II

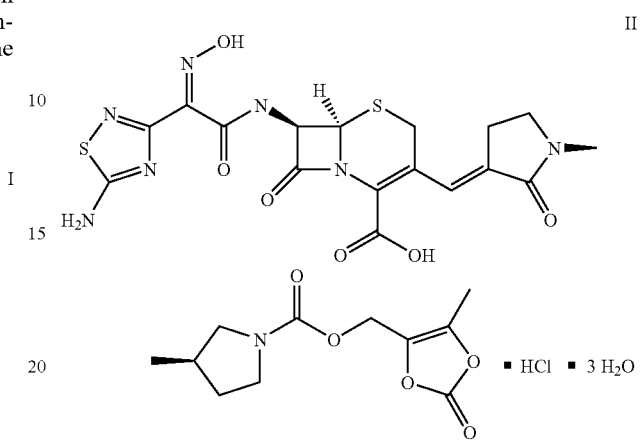

The present invention also relates to cephalosporin in crystalline form of formula I and II.

Further, the present invention relates to a cephalosporin in crystalline form having peaks at the diffraction angles at degrees 2θ (CuK$_\alpha$ radiation) shown in table 1 (see below) in its powder X-ray diffraction pattern:

| diffraction angle 2θ (°) | Relative Intensity |
| --- | --- |
| 6.9 | (m) |
| 7.3 | (s) |
| 9.3 | (m) |
| 9.8 | (w) |
| 11.5 | (m) |
| 13.1 | (m) |
| 13.8 | (w) |
| 14.5 | (vs) |
| 14.9 | (m) |
| 15.4 | (m) |
| 15.7 | (m) |
| 16.6 | (m) |
| 17.2 | (m) |
| 18.2 | (m) |
| 18.5 | (m) |
| 18.7 | (m) |
| 19.2 | (w) |
| 19.6 | (m) |
| 20.3 | (m) |
| 20.9 | (s) |
| 21.4 | (m) |
| 21.8 | (m) |
| 22.2 | (s) |
| 22.7 | (s) |
| 23.0 | (m) |
| 24.8 | (m) |
| 27.1 | (m) |
| 28.6 | (m) |

(vs) = very strong;
(s) = strong;
(m) = medium;
(w) = weak;
(vw) = very weak

It has to be understood that due to small changes in the experimental details, small deviations in the 2θ-values of the characteristic peaks in the X-ray powder diffraction patterns may occur.

The present invention also relates to a process for the preparation of cephalosporin which process comprises
a) mixing an acid and an organic solvent, and adding the solution to cephalosporin of formula III, and stirring the mixture; or
b) mixing an acid and an organic solvent, and adding cephalosporin of formula III to the solution, and stirring the mixture; or
c) suspending cephalosporin of formula III in water and an acid and stirring the mixture.

Further, the present invention relates to a cephalosporin obtainable by the process mentioned above.

The present invention also relates to compositions comprising cephalosporin as mentioned above.

Further, the present invention relates to cephalosporin compounds as mentioned above as medicament.

The present invention also relates to the use of cephalosporin compounds as mentioned above for the preparation of a medicament for use as antiinfectiva.

Further, the present invention relates to formulations of above mentioned cephalosporin with:
1) basic salts (e.g. carbonate, hydrogen carbonate). The use of co-solvents such as PEG, PPG, ethanol, propylene glycol, benzyl alcohol or mixtures thereof.
2) The use of buffers and in-situ salt formers (e.g. citrate, acetate, phosphate, carbonate, lysine, arginine, tromethamin, meglumine, ethylenediamine, triethanolamine) alone or in combination or with co-solvents or basic salts as described in 1).
3) The use of complexing agents (e.g. PVP, cyclodextrines, dextrose) alone or in combination with principles as described in 1) and 2).
4) The use of surfactants (e.g. polysorbate, pluronic, lecithin) alone or in combinations with principles as described in 1), 2) and 3).
5) The principles described in 1), 2), 3) and 4) may apply in direct combination or as separate principle such as an reconstitution solution, used for reconstitution of the cephalosporin salt/s.

The present invention also relates to compositions containing amorphous parts of cephalosporin of formula I and/or II and amorphous parts of cephalosporin of formula III, and crystalline parts of cephalosporin of formula II to sum up to 100%.

Further, the present invention also relates to the use of said cephalosporin in crystalline form alone or in combination with other compounds or formulations of said cephalosporin in crystalline form as antibiotic compounds.

The present invention also relates to a pharmaceutical preparation containing a compound as described above and a therapeutically inert carrier, particularly for the treatment and prophylaxis of infectious diseases.

The term "crystallinity" or "crystalline" is used to describe the part of crystalline material compared to amorphous material and is estimated e.g. by the line shape and the background intensity in XRPD patterns as well as from DSC measurements.

According to these methods, a crystallinity of 90% to 100% is estimated. In a more preferred embodiment the crystallinity is within the range of 92% to 100%. In the most preferred embodiment the crystallinity is within the range of 95% to 100%.

The process for the preparation of compound of formula II may be carried out in either an acid dissolved in organic solvents, an acid or in aqueous acid solutions. Preferred the process is carried out in aqueous acid solutions.

The term "acid", as used within the present invention, means an acids, such as HBr or HCl, preferred HCl. The acid may be used in gaseous form or in dissolved (either in aqueous solution or in an organic solvent) form.

The term "organic solvents" as used within the present invention, means organic solvents such as $C_{1-4}$-alkanol ($CH_3OH$, $C_2H_5OH$, n-$C_3H_7OH$, i-$C_3H_7OH$, i-$C_4H_9OH$, n-$C_4H_9OH$, sec-$C_4H_9OH$), ketones (aceton, ethylmethylketone), ethers (THF, Dioxan) acetonitrile, preferably $CH_3OH$, $C_2H_5OH$, n-$C_3H_7OH$, i-$C_3H_7OH$, i-$C_4H_9OH$, n-$C_4H_9OH$, sec-$C_4H_9OH$, acetone or acetonitrile, most preferred MeOH.

The term "acid solution" as used within the present invention, means HBr or HCl solutions, preferably aqueous HBr or HCl. The aqueous HCl solution in the concentration range of 1% to 30%, more preferred in the concentration range of 5% to 25%, most preferred in the concentration range of 10% to 20%. The aqueous HBr solution in the concentration range of 1% to 62%, more preferred in the concentration range of 5% to 55%, most preferred in the concentration range of 8% to 20%.

The compound of formula I, II and III are useful as antibiotics having potent and broad antibacterial activity; especially against methicillin resistant *Staphylococci* (MRSA) and *Pseudomonas aeruginosa*.

Experimental Part:

Crystallization from acid-saturated organic solvents:

The sodium salt of cephalosporin of formula III was prepared according to the methods described in EP 1087980 and EP 0849269.

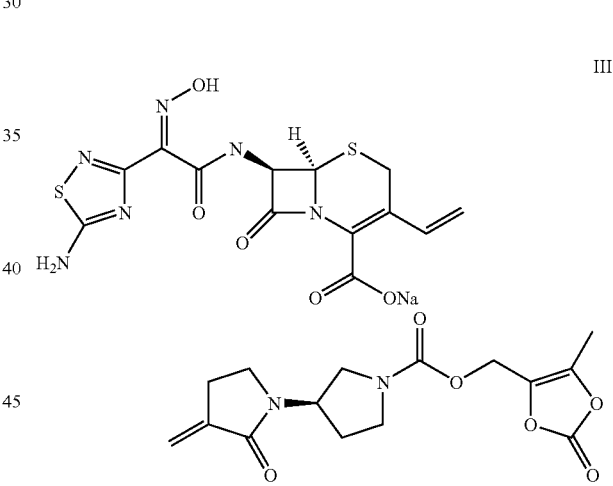

III

The crystallization experiments were carried out in that the acid (either in gaseous form or aqueous solution; preferred HBr or HCl; more preferred HCl) was dissolved in organic solvents as defined above (most preferred methanol), and the solution was added to the cephalosporin of formula III and stirred up to 24 hours (preferably 3-20 hours, most preferred 4-7 hours). The resulting suspension is filtered, washed with an organic solvent (preferably acetone) and dried in an air flow for a few minutes.

TABLE 2

| No. | Compound III | Solvent | Yield | Result |
|---|---|---|---|---|
| 1 | 60.8 mg | 5 ml MeOH, HCl saturated 1 ml water, 23° C. | 32 mg | Crystalline |
| 2 | 60.8 mg | 6 ml MeOH, HCl saturated, 23° C. | 25 mg | Crystalline |

TABLE 2-continued

| No. | Compound III | Solvent | Yield | Result |
|---|---|---|---|---|
| 3 | 103 mg | 15 ml MeOH, HCl saturated (room temperature) | 73 mg | Crystalline |

The reaction is carried out at a temperature in the range of 0-30° C., preferred 5-25° C., most preferred 15-25° C.

The crystalline material obtained contained at least 50% of crystalline material.

Crystallization experiments led, according to DSC, elemental microanalytics, X-ray powder diffraction and Raman spectroscopy, to a crystalline cephalosporin of formula II.

The following examples and FIG. 1 are provided to aid the understanding of the present invention.

FIG. 1 shows Powder X-ray Diffraction Pattern of crystalline form of cephalosporin of formula II (CuK$_\alpha$ radiation)

Crystallization from Acid Solution

The following table shows a series of crystallization experiments in suspension.

The crystallization experiments were carried out in that cephalosporin of formula III is suspended in water and an acid (in gaseous form or in aqueous solution; preferred HBr or HCl; more preferred HCl). The resulting suspension is stirred up to 24 hours (preferably 3-20 hours, most preferred 4-7 hours), filtered, washed with an organic solvent (preferably acetone) and dried in an air flow for a few minutes.

TABLE 3

| No. | Compound III | Solvent | Yield* | Result |
|---|---|---|---|---|
| 4 | 100 mg | 1.6 ml water + 0.4 ml HBr (48% in water) | 40 mg | Crystalline |
| 5 | 61 mg | 0.3 ml water + 6 ml HCl (25%) additionally 4 × 1 ml water, 23° C. | 27 mg | Crystalline |
| 6 | 112 mg | 0.5 ml water + 10 ml HCl (25%), 15° C. | 56 mg | Crystalline |
| 7 | 69 mg | 0.3 ml water + 4 ml HCl (25%), 20° C. + 4 ml HCl (32%), 20° C. | 26 mg | Crystalline |
| 8 | 81 mg | 1.4 ml water + HCl (25%), 23° C. | 49 mg | Crystalline |
| 9 | 201 mg | 20 ml HCl (7.4%/2 N), 23° C. | 181 mg | Crystalline |
| 10 | 151 mg | 30 ml HCl (12.5%), 23° C. | 136 mg | Crystalline |
| 11 | 150 mg | 30 ml HCl (12.5%), 5° C. | 187 mg | Crystalline |
| 12 | 150 mg | 15 ml HCl (12.5%), 20° C. | 161 mg | Crystalline |
| 13 | 150 mg | 30 ml HCl (7.4%/2 N), 23° C. | 125 mg | Crystalline |
| 14 | 100 mg | 50 ml HCl (7.4%/2 N), 23° C. | 70 mg | Crystalline |
| 15 | 101 mg | 25 ml water, 25 ml HCl (25%), 23° C. | 81 mg | Crystalline |
| 16 | 102 mg | 50 ml HCl (12.5%), 23° C. | 82 mg | Crystalline |
| 17 | 202 mg | 20 ml HCl (7.4%/2 N), 15° C. | 186 mg | Crystalline |

*yield = mass after filtration, regardless of salt or hydrate formation, residual solvent (water) can not be excluded The reaction is carried out at a temperature in the range of 0-30° C., preferred 5-25° C., most preferred 15-25° C.

Crystallization experiments led, according to DSC elemental microanalytics and X-ray powder diffraction, to a crystalline cephalosporin of formula II.

Methods of Characterizing the Cephalosporin Material:

Dynamic vapor sorption:

In general, the DVS measurement indicates the investigated crystalline sample exists as a trihydrate form.

Elemental Microanalytics

Elemental microanalytics to demonstrate the existence (6R,7R)-7-[(Z)-2-(5-Amino-[1,2,4]thiadiazol-3-yl) -2-hydroxyimino-acetylamino]-8-oxo-3-[(E)-(R)-1'-(5-methyl-2-oxo-[1,3]dioxol-4-ylmethoxycarbonyl)-2-oxo-[1,3']bipyrrolidinyl-3-ylidenemethyl]-8-oxo5-thia-1-aza-bicyclo[4.2.0] oct-2-ene-2-carboxylic acid Hydrochloride Trihydrate

TABLE 4

Analytical results of the investigated sample no. 17 (compound II) are summarized below:

| | element | | | | | |
|---|---|---|---|---|---|---|
| | C | H | N | S | Cl | O |
| atomic weight | 12.01 | 1.00 | 14.01 | 32.07 | 35.45 | 16.00 |
| number of atoms | 26 | 33 | 8 | 2 | 1 | 14 |
| mr(atoms) | 312.26 | 33.00 | 112.08 | 64.14 | 35.45 | 224.00 |
| nominal % | 39.99 | 4.23 | 14.35 | 8.21 | 4.54 | 28.68 |
| found % | 39.23 | 4.20 | 14.06 | 7.86 | 4.56 | 29.20 |
| difference % | −1.89 | −0.61 | −2.04 | −4.30 | 0.45 | 1.80 |

Total mass: 780.93 assuming the composition $C_{26}H_{26}N_8O_{11}S_2 \cdot HCl \cdot 3\ H_2O$ Methods of proving/characterizing the presence of crystalline parts in the prepared cephalosporin material:

Differential Scanning Calorimetry (DSC):

DSC measurements were used to identify amorphous parts in samples of the HCl-salt.

DSC Investigation and X-ray Powder Diffraction of Selected Samples

Selected samples have been investigated by DSC with respect to amorphous parts being present. In principle, two different kind of samples were found: on the one hand samples showing decomposition between about 100° C. and 140° C., on the other hand a set of samples is characterized by an endothermic peak at about 149° C. and simultaneous decomposition.

Samples with an endothermic heat flow and presumably very small amorphous parts according to DSC were further investigated by X-ray powder diffraction. In general, these samples showed similar diffraction patterns but differed in the grade of crystallinity.

Determination of Storage Stability of Crystalline Material of Formula I

A crystalline and an amorphous sample of (6R,7R)-7-[(Z)-2-(5-Amino-[1,2,4]thiadiazol-3-yl)-2-hydroxyimino-acetylamino]-8-oxo-3-[(E)-(R)-1'-(5-methyl-2-oxo-[1,3]dioxol-4-ylmethoxycarbonyl)-2-oxo-[1,3']bipyrrolidinyl-3-ylidenemethyl]-8-oxo-5-thia-1-aza-bicyclo[4.2.0]oct-2-ene-2-carboxylic acid were stored at different temperatures for 24 hours, 28 days and for 3 months. Results of HPLC analysis are summarized in table 4 to table 6.

TABLE 5

Storage of amorphous compound I and crystalline compound II for 24 hours

| Temperature | Rel. Humidity | Area-% (HPLC) amorphous compound I | Area-% (HPLC) crystalline compound II |
|---|---|---|---|
| −20° C. | Not defined | 99.04 | 95.77 |
| 5 | Ca. 58% | 99.05 | 95.7 |
| 25 | Ca. 58% | 98.85 | 95.75 |
| 40 | Ca. 75% | 98.25 | 95.45 |
| 60 | Ca. 75% | 96.67 | 95.57 |

TABLE 6

Storage of amorphous compound I and crystalline compound II for 28 days

| Temperature | Rel. Humidity | Area-% (HPLC) amorphous compound I | Area-% (HPLC) crystalline compound II |
|---|---|---|---|
| −20° C. | Not defined | 98.6 | 95.3 |
| 5 | Ca. 58% | 98.1 | 95.2 |
| 25 | Ca. 58% | 96.4 | 94.9 |

TABLE 7

Storage of amorphous compound I and crystalline compound II for 3 months

| Temperature | Rel. Humidity | Area-% (HPLC) amorphous compound I | Area-% (HPLC) crystalline compound II |
|---|---|---|---|
| −20° C. | Not defined | 97.6 | 94 |
| 5 | Ca. 58% | 96.9 | 93.9 |
| 25 | Ca. 58% | 91.4 | 93.4 |

Storage for 24 hours revealed a very good stability of the crystalline compound II in the whole temperature range of investigation. The amorphous compound I decomposed significantly at temperatures above 5° C.

During 28 days a slight decomposition of crystalline compound II was observed at 25° C. In comparison, the content of compound I in the amorphous compound I decreased at 5° C. and even stronger at 25° C.

After 3 months, the amorphous compound I showed a slight decomposition even at 5° C. The content of amorphous compound I strongly decreased at 25° C. In contrast, the crystalline compound II showed no decomposition at 5° C. as compared to −20° C. at 25° C. a slight decomposition was observed.

The products in accordance with the invention can be used as medicaments, for example, in the form of pharmaceutical preparations for enteral (oral) administration. The products in accordance with the invention can be administered, for example, perorally, such as in the form of tablets, coated tablets, dragees, hard and soft gelatine capsules, solutions, emulsions or suspensions, or rectally, such as in the form of suppositories.

Pharmaceutical compositions containing these compounds can be prepared using conventional procedures familiar to those skilled in the art, such as by combining the ingredients into a dosage form together with suitable, non-toxic, inert, therapeutically compatible solid or liquid carrier materials and, if desired, the usual pharmaceutical adjuvants.

It is contemplated that the compounds are ultimately embodied into compositions of suitable oral or parenteral dosage forms. The compositions of this invention can contain, as optional ingredients, any of the various adjuvants which are used ordinarily in the production of pharmaceutical preparations. Thus, for example, in formulating the present compositions into the desired oral dosage forms, one may use, as optional ingredients, fillers, such as coprecipitated aluminum hydroxide, calcium carbonate, dicalcium phosphate, mannitol or lactose; disintegrating agents, such as maize starch; and lubricating agents, such as talc, calcium stearate, and the like. It should be fully understood, however, that the optional ingredients herein named are given by way of example only and that the invention is not restricted to the use hereof. Other such adjuvants, which are well known in the art, can be employed in carrying out this invention.

Suitable as such carrier materials are not only inorganic, but also organic carrier materials. Thus, for tablets, coated tablets, dragees and hard gelatine capsules there can be used, for example, lactose, maize starch or derivatives thereof, talc, stearic acid or its salts. Suitable carriers for soft gelatine capsules are, for example, vegetable oils, waxes, fats and semi-solid and liquid polyols (depending on the nature of the active substance; no carriers are, however, required in the case of soft gelatine capsules). Suitable carrier materials for the preparation of solutions and syrups are, for example, water, polyols, saccharose, invert sugar and glucose. Suitable carrier materials for suppositiories are, for example, natural or hardened oils, waxes, fats and semi-liquid or liquid polyols.

As pharmaceutical adjuvants there are contemplated the usual preservatives, solubilizers, stabilizers, wetting agents, emulsifiers, sweeteners, colorants, flavorants, salts for varying the osmotic pressure, buffers, coating agents and antioxidants.

The products in accordance with the invention can be used as medicaments, for example, in the form of pharmaceutical preparations for parenteral administration, and for this purpose are preferably made into preparations as lyophilisates or dry powders for dilution with customary agents, such as water or isotonic common salt or carbohydrate (e.g. glucose) solution.

Depending on the nature of the pharmacologically active compound the pharmaceutical preparations can contain the compound for the prevention and treatment of infectious diseases in mammals, human and non-human, a daily dosage of about 10 mg to about 4000 mg, especially about 50 mg to about 3000 mg, is usual, with those of ordinary skill in the art appreciating that the dosage will depend also upon the age, conditions of the mammals, and the kind of diseases being prevented or treated. The daily dosage can be administered in a single dose or can be divided over several doses. An average single dose of about 50 mg, 100 mg, 250 mg, 500 mg, 1000 mg, and 2000 mg can be contemplated.

The invention claimed is:

1. A cephalosporin compound in crystalline form, wherein the cephalosporin compound is a hydrobromide salt of the cephalosporin of formula I

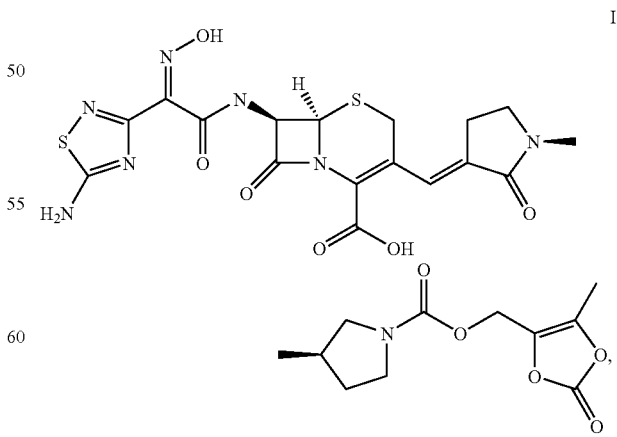

a hydrate of the hydrobromide salt of said cephalosporin, or a hydrate of a hydrochloride salt of said cephalosporin.

2. The cephalosporin compound in crystalline form of claim 1, wherein the cephalosporin compound is the hydrochloride hydrate or hydrobromide hydrate.

3. The cephalosporin compound in crystalline form of claim 2, wherein the cephalosporin compound is the hydrochloride hydrate.

4. The cephalosporin compound in crystalline form of claim 3, wherein the cephalosporin compound is a cephalosporin salt hydrate of formula II

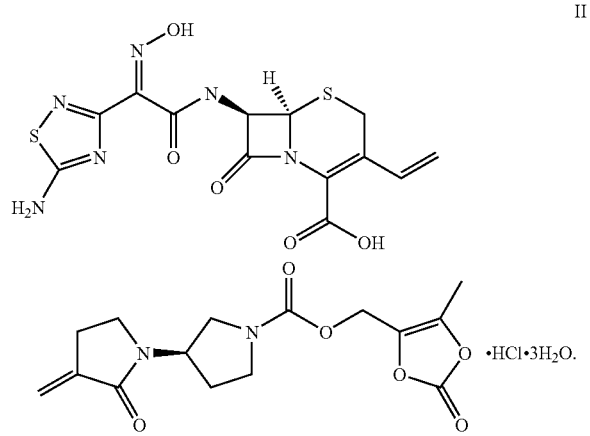

5. The cephalosporin compound in crystalline form of claim 4, which shows the peaks at the diffraction angles shown in the following table in its powder X-ray diffraction pattern (CuK$_\alpha$ radiation):

| diffraction angle 2θ(°) | Relative Intensity |
| --- | --- |
| 6.9 | (m) |
| 7.3 | (s) |
| 9.3 | (m) |
| 9.8 | (w) |
| 11.5 | (m) |
| 13.1 | (m) |
| 13.8 | (w) |
| 14.5 | (vs) |
| 14.9 | (m) |
| 15.4 | (m) |
| 15.7 | (m) |
| 16.6 | (m) |
| 17.2 | (m) |
| 18.2 | (m) |
| 18.5 | (m) |
| 18.7 | (m) |
| 19.2 | (w) |
| 19.6 | (m) |
| 20.3 | (m) |
| 20.9 | (s) |
| 21.4 | (m) |
| 21.8 | (m) |
| 22.2 | (s) |
| 22.7 | (s) |
| 23.0 | (m) |
| 24.8 | (m) |
| 27.1 | (m) |
| 28.6 | (m) | wherein (vs) is very strong; (s) is strong; (m) is medium; (w) is weak; and (vw) is very weak.

6. The cephalosporin compound in crystalline form of claim 4, having the X-ray powder diffraction pattern set forth in the FIG. 1.

* * * * *

UNITED STATES PATENT AND TRADEMARK OFFICE
CERTIFICATE OF CORRECTION

PATENT NO. : 7,531,650 B2  Page 1 of 1
APPLICATION NO. : 10/547648
DATED : May 12, 2009
INVENTOR(S) : Joerg Berghausen It is certified that error appears in the above-identified patent and that said Letters Patent is hereby corrected as shown below:

In ABSTRACT cover page, column 2, line 6 of Abstract, please change

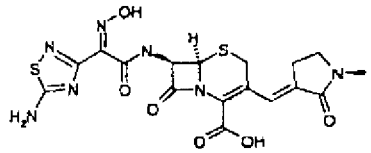

to

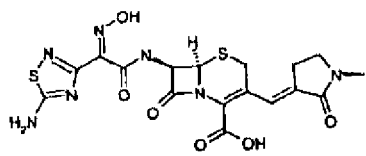

In Column 8, line 50, (claim 1, line 4) please change

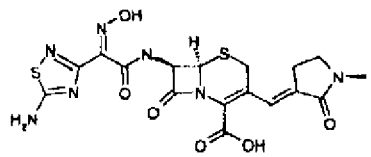

to read

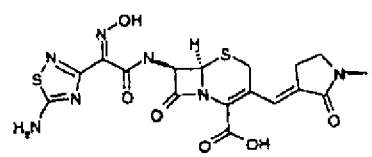

Signed and Sealed this

First Day of December, 2009

David J. Kappos
*Director of the United States Patent and Trademark Office*